United States Patent
Merrell

(10) Patent No.: US 10,517,803 B2
(45) Date of Patent: Dec. 31, 2019

(54) INDIVIDUAL'S SENSITIVITY TO FLUORIDE POISONING

(71) Applicant: Scott Peterson Merrell, Norwalk, CT (US)

(72) Inventor: Scott Peterson Merrell, Norwalk, CT (US)

(*) Notice: Subject to any disclaimer, the term of this patent is extended or adjusted under 35 U.S.C. 154(b) by 0 days.

(21) Appl. No.: 15/808,104

(22) Filed: Nov. 9, 2017

(65) Prior Publication Data
US 2019/0133899 A1    May 9, 2019

(51) Int. Cl.
| | |
|---|---|
| *A61K 8/18* | (2006.01) |
| *A61Q 11/00* | (2006.01) |
| *A23L 33/00* | (2016.01) |
| *A23L 33/16* | (2016.01) |
| *A23L 33/125* | (2016.01) |

(52) U.S. Cl.
CPC .............. *A61K 8/18* (2013.01); *A23L 33/125* (2016.08); *A23L 33/16* (2016.08); *A23L 33/30* (2016.08); *A23L 33/40* (2016.08); *A61Q 11/00* (2013.01); *A23V 2002/00* (2013.01); *A61K 2800/30* (2013.01)

(58) Field of Classification Search
CPC ........................................................ A61K 8/18
See application file for complete search history.

(56) References Cited

U.S. PATENT DOCUMENTS 5,716,600 A * 2/1998 Zahradnik ............... A61K 8/21
424/49
2014/0374357 A1* 12/2014 Roy ........................ C02F 1/286
210/670

OTHER PUBLICATIONS

ADA fluoridation guide, 2005.*
Luoma (Int Dent J. Mar. 1985;35(1):43-9).*
Levy et al (Cancer Epidemiology, vol. 36, Issue 2, Apr. 2012, pp. e83-e88). (Year: 2012).*
Blaylock, Fluoride 2004;37(4):264-277 Research Report. (Year: 2004).*
Levy et al, J of Public Heath Densitry, vol. 55, Iss 1, 1995, 39-52. (Year: 1995).*
International Search Report and Written Opinion of the International Searching Authority issued in International Application No. PCT/US18/57345 dated Nov. 30, 2018.

* cited by examiner

*Primary Examiner* — Benjamin J Packard
(74) *Attorney, Agent, or Firm* — Wenderoth, Lind & Ponack, L.L.P.

(57) ABSTRACT

The present invention relates to a method for preventing or treating disease in a mammal, particularly a human, by maintaining a fluoride free diet. Such diseases include autism, cancer, Alzheimer's disease, multiple sclerosis, calcification of the pineal gland, diabetes, depression, schizophrenia, psychotic diseases, muscular dystrophy, and others.

6 Claims, No Drawings

INDIVIDUAL'S SENSITIVITY TO FLUORIDE POISONING

TECHNICAL FIELD

The present invention relates to a method for preventing or treating disease in a mammal, particularly a human, by maintaining a fluoride free diet. Many diseases can result from fluoride poisoning, including autism, cancer, Alzheimer's disease, multiple sclerosis, calcification of the pineal gland, diabetes, depression, schizophrenia, psychotic diseases, muscular dystrophy, and others. By maintaining a fluoride free diet, an individual may treat an existing disease condition and/or prevent development of such diseases.

BACKGROUND ART

Water fluoridation in the United States began in 1945 in Grand Rapids, Mich. The city adjusted the fluoride content of its water supply to 1.0 ppm. The city became the first city in the United States to implement community water fluoridation. Since then, the public water supply of most cities in the United States supplies fluoridated water to its population. At the same time, rates of health problems and disease have also risen, such as autism, cancer, Alzheimer's disease, multiple sclerosis, calcification of the pineal gland, diabetes, depression, schizophrenia, psychotic diseases, muscular dystrophy, and others.

Fluoride is a poison. According to the U.S. Department of Agriculture, the Dietary Reference Intakes, which is the "highest level of daily nutrient intake that is likely to pose no risk of adverse health effects", specify 10 mg/day for most people, corresponding to 10 L of fluoridated water with no risk. For infants and young children, the values are smaller, ranging from 0.7 mg/d for infants to 2.2 mg/d. Water and food sources of fluoride include community water fluoridation, fluoride teeth treatments, seafood, tea, and gelatin.

Fluorides are medically categorized as "protoplasmic poisons". The Journal of the American Medical Association (Sep. 18, 1943) stated "Fluorides are general protoplasmic poisons, changing the permeability of the cell membrane by inhibiting certain enzymes. The exact mechanism of such actions are obscure."

Soluble fluoride salts, of which sodium fluoride is the most common, are toxic, and have resulted in both accidental and self-inflicted deaths from acute poisoning. The lethal dose for most adult humans is estimated at 5 to 10 g (which is equivalent to 32 to 64 mg/kg elemental fluoride/kg body weight). A case of a fatal poisoning of an adult with 4 grams of sodium fluoride is documented, and a dose of 120 g sodium fluoride has been survived. For sodium fluorosilicate ($Na_2SiF_6$), the median lethal dose ($LD_{50}$) orally in rats is 0.125 g/kg, corresponding to 12.5 g for a 100 kg adult.

The time period for causing a fatality ranges from 5 min to 12 hours. The mechanism of toxicity involves the combination of the fluoride anion with the calcium ions in the blood to form insoluble calcium fluoride, resulting in hypocalcemia. Calcium is indispensable for the function of the nervous system, and the condition of hypocalcemia, i.e. low calcium levels in the blood serum, can be fatal.

A possible relationship between fluoridated drinking water and cancer and other diseases has been debated for years. Most studies have concluded that there is no credible evidence of a link between fluoridated water and an increased risk of cancer. However these studies did not study the long term effect of fluoride ingestion. Nor did the studies evaluate the sensitivity of certain individuals to fluoride poisoning compared to the general population. The studies only examined effects on the general population.

Pineal gland calcification is known to be caused by exposure to fluoride. The human pineal gland is outside the blood brain barrier. Fluoride accumulates and calcifies in the pineal gland, thereby interfering with the normal function of the pineal gland. See Jennifer Luke, Fluoride Deposition in the Aged Human Pineal Gland, Caries Res 2991; 35: 1125-1128 (2001). The extent of pineal calcification varies between individuals, ranging from 4,600 to 37,500 mg Ca/kg wet weight. Some research has shown that 100% of multiple sclerosis patients have calcified pineal glands.

SUMMARY OF THE INVENTION

The present invention is directed to preventing or treating disease in a mammal, particularly a human. The present inventor has conducted extensive research, and has concluded that certain individuals have a sensitivity to fluoride, and that such sensitivity may take years or decades to manifest any symptoms. These individuals are at increased risk of developing cancer and other diseases. To prevent development of such diseases, or to treat an existing disease, the method of the invention involves a reduction, and preferably an elimination, of fluoride from the individual's diet.

DETAILED DESCRIPTION OF INVENTION

All individuals diagnosed with any form of cancer should be placed on a fluoride free diet.

All individuals diagnosed with autism should be placed on a fluoride free diet.

All senior citizens diagnosed with Alzheimer's disease should be placed on a fluoride free diet.

All individuals diagnosed with multiple sclerosis should be placed on a fluoride free diet.

All individuals diagnosed with muscular dystrophy should be placed on a fluoride free diet.

All individuals diagnosed with calcification of the pineal gland, diabetes, depression, schizophrenia, psychotic diseases, and other diseases should be placed on a fluoride free diet.

Individuals desiring to avoid the risk of developing autism, cancer, Alzheimer's disease, multiple sclerosis, calcification of the pineal gland, diabetes, depression, schizophrenia, psychotic diseases, muscular dystrophy, and other diseases should be placed on a fluoride free diet.

All pregnant women should be placed on a fluoride free diet.

All children should be placed on a fluoride free diet.

The inventor advocates a Three Step Program for a healthy fluoride free diet.

The first step is to stop using toothpaste which contains fluoride. The individual should switch to baking soda or any fluoride free toothpaste. The individual should also refrain from having fluoride teeth treatments, and gargling with fluoride mouthwashes, which are designed for preventing cavities.

The second step is to stop drinking and cooking with fluorinated drinking water. The individual may switch to fluoride free bottled water. Alternatively, the individual may drink or cook with tap water which has been passed through a charcoal filter. Food should be prepared with fluoride free water.

The third step is to eliminate artificial sweeteners from the diet and use only natural brown sugar.

In addition to the Three Step Program, the inventor recommends using iodized table salt (NaCl) in the individual's diet. Iodized table salt can remove sodium fluoride from the individual's system over time. The individual should use no more iodized salt than that recommended for daily use.

The reason why fluoride poisoning may cause disease in certain individuals while not affecting the general population is generally unknown. However this is not a unique situation. It is unknown why some individuals develop lung cancer from smoking over 5-10 years, while other individuals never develop lung cancer after a lifetime of smoking. Similarly, it is unknown why some individuals develop liver cirrhosis over 5-10 years, while other individuals do not regardless of the amount of alcohol the individual consumes. The fact remains that some diseases take a long time to develop. Moreover, certain individuals have a greater sensitivity to poisons than other individuals.

The inventor has a theory (the Merrell Female Sex Cell Theory) as to the possible mechanism of some diseases caused by fluoride poisoning, particularly ovarian cancer and autism. Without being bound to any particular theory, it is the inventor's theory that certain female sex cells may have an inherent sensitivity to fluoride poisoning. Human female sex cells are created during the fetal development stage inside the womb. By the time the female conceives a child, the female sex cells have been subjected to 20-30 years of fluoride contact via the blood stream. This extended fluoride contact on the female sex cells may result in a disease condition affecting the embryo, in the case where the female sex cells have greater sensitivity to fluoride than the average female sex cells.

Children are more vulnerable to fluoride poisoning than adults. There is no fluoride toothpaste containing a child's supply of fluoride. Children use the same toothpaste, in the same amount, as adults use. Yet it is well recognized even by the general medical community as noted above that the maximum safe amounts of fluoride for children are much less than the safe amounts of fluoride for an adult person. Combine the fluoride levels ingested by a child from toothpaste, with the fluoride applied to children's teeth for cavity prevention, coupled with fluoride containing water, and it is apparent that fluoride ingestion by children creates a significantly greater risk than it does to an adult male.

For purposes of this application, the inventor defines a child as a male or female from 1 year to less than 18 years of age. The inventor defines an adult as a male or female from 18 years or older. The inventor also defines the individual's "diet" as encompassing any means by which an individual might ingest fluoride from any source, such as including but not limited to fluoride contained in food, water, toothpaste, mouthwashes, tooth sealants, vitamins, tablets, compositions, etc.

The ancient Romans poisoned themselves by using the wrong metal, lead, for their drinking water pipes and cooking pots. They thought that lead enhanced the flavor of the drink. It was not recognized that lead was a poison. Similarly, we are creating various diseases by using the poison fluoride in the nation's water supply and other sources. It is not recognized by the general medical community that fluoride is the cause of many diseases in individuals having a sensitivity to fluoride.

Fluoride poisoning also causes premature aging of the skin in men and women. If a person goes on a fluoride free diet, the person's skin will appear younger and healthier over time.

I claim:

1. A method for treating a disease caused by fluoride in a human individual, which comprises the steps of:
   (a) eliminating fluoride from the human individual's diet,
   (b) using only natural brown sugar as a sweetener in the individual's diet,
   (c) using iodized salt as a salt source in the individual's diet,
   wherein the disease is autism, cancer, Alzheimer's disease, multiple sclerosis, calcification of the pineal gland, diabetes, depression, schizophrenia, psychotic diseases, or muscular dystrophy, and
   wherein the disease is improved by treating the human individual by the steps (a), (b) and (c).

2. The method of claim 1, which comprises the step of using only a fluoride free toothpaste.

3. The method of claim 1, which comprises the step of drinking and consuming only fluoride free water.

4. The method of claim 1, wherein the individual is an adult male, an adult female, a male child, or a female child.

5. The method of claim 1, wherein the human individual has a sensitivity to fluoride which causes the individual to have an increased risk of the developing the disease.

6. The method of claim 1, wherein the human individual is a child.

* * * * *